US009854656B2

(12) United States Patent
Göderer et al.

(10) Patent No.: US 9,854,656 B2
(45) Date of Patent: Dec. 26, 2017

(54) DETECTION OF X-RAY RADIATION (71) Applicant: Siemens Aktiengesellschaft, Munich (DE)

(72) Inventors: Edgar Göderer, Forchheim (DE); Steffen Kappler, Effeltrich (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 474 days.

(21) Appl. No.: 14/476,808

(22) Filed: Sep. 4, 2014

(65) Prior Publication Data
US 2015/0078512 A1 Mar. 19, 2015

(30) Foreign Application Priority Data

Sep. 18, 2013 (DE) .......................... 10 2013 218 692

(51) Int. Cl.
*A61B 6/03* (2006.01)
*G01T 1/36* (2006.01)
(Continued)

(52) U.S. Cl.
CPC ............... *H05G 1/58* (2013.01); *A61B 6/032* (2013.01); *A61B 6/4241* (2013.01);
(Continued)

(58) Field of Classification Search
CPC ....... A61B 6/032; A61B 6/4241; A61B 6/482; A61B 6/5258; A61B 6/542; A61B 6/545;
(Continued)

(56) References Cited

U.S. PATENT DOCUMENTS 9,207,332 B2 * 12/2015 Spahn ....................... G01T 1/17
2005/0123090 A1   6/2005 Heismann
(Continued)

FOREIGN PATENT DOCUMENTS

CN    1627100 A    6/2005
CN  101542316 A    9/2009
(Continued)

OTHER PUBLICATIONS

R. Ballabriga,"The Medipix3 Prototype, a Pixel Readout Chip Working in Single Photon Counting Mode with Improved Spectrometric Performance", 2006, 5pgs, 2006 IEEE Nuclear Science Symposium Conference Record.
(Continued)

*Primary Examiner* — Thomas R Artman
(74) *Attorney, Agent, or Firm* — Harness, Dickey & Pierce, P.L.C.

(57) ABSTRACT

An X-ray detector is disclosed, including a detection unit to generate a detection signal for incident X-ray radiation; a signal analysis module to determine a set of count rates for incident X-ray radiation based upon the detection signal and signal analysis parameters for X-ray radiation; and a switchover control unit for switching between first signal analysis parameters and second signal analysis parameters. When an amount of X-ray radiation is incident on the detection module, a first set of count rates is generated for a first time interval based upon first signal analysis parameters and a second set of count rates is generated for a second time interval based upon second signal analysis parameters, different from the first signal analysis parameters. An X-ray imaging system including the detector; a method for determining count rates for X-ray radiation; and a method for calibrating signal analysis parameters are also disclosed.

20 Claims, 5 Drawing Sheets

(51) Int. Cl.
  *G01N 23/04*   (2006.01)
  *H05G 1/58*   (2006.01)
  *A61B 6/00*   (2006.01)
  *G01T 1/17*   (2006.01)

(52) U.S. Cl.
  CPC ............. *G01N 23/046* (2013.01); *G01T 1/17* (2013.01); *G01T 1/36* (2013.01)

(58) Field of Classification Search
  CPC ...... A61B 6/582; A61B 6/585; G01N 23/087; G01N 2223/304; G01N 2223/423
  See application file for complete search history.

(56) References Cited

U.S. PATENT DOCUMENTS

| | | | |
|---|---|---|---|
| 2008/0099689 A1* | 5/2008 | Nygard | G01T 1/2018 250/370.09 |
| 2009/0147919 A1 | 6/2009 | Goto et al. | |
| 2010/0027738 A1 | 2/2010 | Carmi | |
| 2010/0316184 A1 | 12/2010 | Iwanczyk | |
| 2011/0096892 A1 | 4/2011 | Forthmann et al. | |
| 2011/0142194 A1 | 6/2011 | Toth | |
| 2011/0147599 A1 | 6/2011 | Grobshtein | |
| 2012/0085915 A1* | 4/2012 | Baeumer | G01T 1/17 250/370.09 |
| 2012/0305757 A1 | 12/2012 | Kappler | |
| 2014/0016748 A1* | 1/2014 | Spahn | G01T 1/247 378/62 |
| 2015/0078512 A1* | 3/2015 | Goderer | G01N 23/046 378/19 |
| 2015/0090893 A1* | 4/2015 | Spahn | G01T 1/2928 250/394 |

FOREIGN PATENT DOCUMENTS

| | | |
|---|---|---|
| CN | 102217947 A | 10/2011 |
| CN | 102809756 A | 12/2012 |

OTHER PUBLICATIONS

Chinese Office Action and English translation thereof dated Sep. 26, 2016.

\* cited by examiner

FIG 2

DETECTION OF X-RAY RADIATION

PRIORITY STATEMENT

The present application hereby claims priority under 35 U.S.C. §119 to German patent application number DE 102013218692.4 filed Sep. 18, 2013, the entire contents of which are hereby incorporated herein by reference.

FIELD

At least one embodiment of the present invention generally relates to an X-ray detector for detecting X-ray radiation, the X-ray detector comprising a detection unit which generates a detection signal for X-ray radiation incident on the detection unit and a signal analysis module which, on the basis of the detection signal and predefined signal analysis parameters for X-ray radiation, determines a set of count rates for X-ray radiation incident on the detection unit. At least one embodiment of the invention furthermore generally relates to a method for determining count rates for X-ray radiation by way of such an X-ray detector, as well as to an X-ray imaging system having such an X-ray detector.

BACKGROUND

Two- or three-dimensional image data is often generated with the aid of state-of-the-art imaging methods and such data can be used for visualizing an imaged examination object and in addition also for further applications.

The imaging methods are frequently based on the detection of X-ray radiation, with data referred to as projection measurement data being generated in the process. Projection measurement data can be acquired with the aid of a computed tomography system (CT system), for example. In CT systems, a combination consisting of X-ray source and oppositely positioned X-ray detector is arranged on a gantry and typically rotates around a measurement space in which the examination object (referred to hereinafter without loss of generality as the patient) is situated. In this case the center of rotation (also known as the "isocenter") coincides with an axis referred to as system axis z. In the course of one or more revolutions the patient is irradiated with X-ray radiation of the X-ray source, projection measurement data or X-ray projection data being acquired with the aid of the oppositely disposed X-ray detector.

The generated projection measurement data is dependent in particular on the design of the X-ray detector. X-ray detectors typically have a plurality of detection units which in most cases are arranged in the form of a regular pixel array. Each of the detection units generates a detection signal for X-ray radiation incident on the detection units, which detection signal is analyzed with regard to intensity and spectral distribution of the X-ray radiation at specific time instants in order to obtain inferences in relation to the examination object and to generate projection measurement data.

In this case each specific time instant is assigned a specific angle of rotation of the X-ray source around the isocenter, also known as the projection angle. The projection measurement data associated with a specific projection angle at a specific time instant or specific time interval is typically referred to as a so-called "projection", and the time interval or time instant assigned to a specific projection angle is referred to hereinbelow as the "frame time".

The projection measurement data is acquired with the aid of CT systems commonly in use today and is used for the purpose of reconstructing a set of sectional images (slices) or, as the case may be, a volumetric dataset. Several hundred to several thousand projections are used for each individual sectional image. The time to acquire a projection (also: a "frame") typically amounts to a few hundred microseconds (usually between 100 µs and 1 ms). The frame time is generally determined by the gantry's rotational speed and the rotation angle range in which projection measurement data is to be generated for the volumetric dataset.

In the case of what are termed quanta-counting or photon-counting X-ray detectors, the detection signal for X-ray radiation is analyzed with regard to the intensity and the spectral distribution of the X-ray radiation in the form of count rates. The count rates are made available as output data of what is termed a detector channel which is assigned to one detection unit in each case. With quanta- or photon-counting detectors having a plurality of energy thresholds, each detector channel normally generates a set of count rates per projection on the basis of the respective detection signal of the detection unit. In such cases the set of count rates can include count rates for a plurality of different, in particular simultaneously checked energy threshold values. The energy threshold values and the number of energy thresholds to which an energy threshold value is assigned in each case are in most cases predefined as signal analysis parameters for acquisition of the projection.

In this case an upper limit for the number of simultaneously checked energy thresholds of a detector channel is given in that separate signal comparators and counter elements should be present in each case for each checked energy threshold in the detector channel. For cost and space reasons the number of energy thresholds can therefore not be increased ad infinitum, and consequently compromises in terms of the number of analyzed energy thresholds are unavoidable. It is clear in this case that the signal analysis parameters ultimately determine the quality of the analysis of the X-ray radiation and hence of the generated projection measurement data. The quality of the generated projection measurement data is in this case influenced inter alia by the separation of two X-ray radiation quanta in the detection signal which is possible in a temporal interval referred to as "single pulse separation". Furthermore, the quality of the projection measurement data can also be affected by the energetic interval in which the separation of two X-ray radiation quanta (which is generally represented as voltage distance in the signal) is possible.

All in all, however, it is difficult to specify these signal analysis parameters in a suitable manner in advance so that high-quality projection measurement data can be generated. The present invention provides a remedy in this regard.

SUMMARY

At least one embodiment of the invention is directed to improving projection measurement data with regard to determining X-ray energy and/or intensity. At least one embodiment of the invention is directed to a method by which X-ray imaging as a whole can be improved.

An X-ray detector, a method for determining count rates for X-ray radiation, and a method for calibrating signal analysis parameters of an X-ray detector are disclosed.

According to at least one embodiment of the invention, a quanta-counting or photon-counting X-ray detector comprising a detection unit is proposed which generates a detection signal on the basis of X-ray radiation incident on the detection unit. The detection unit comprises in particular a detection zone in order for example to generate charge pulses as a detection signal for X-ray radiation absorbed by the detection unit. The detection signal and in particular the charge pulses are therefore suitable in particular for determining the energy of the absorbed X-ray radiation.

At least one embodiment of the invention furthermore relates to a method for determining count rates for X-ray radiation by use of an X-ray detector, wherein the signal analysis module is used to generate a first set of count rates for X-ray radiation incident on the detection unit using, i.e. on the basis of, first signal analysis parameters, and in a following step a switchover of the signal analysis module is effected, preferably for the purpose of acquiring an, in particular immediately, succeeding projection, to second signal analysis parameters which are different from the first signal analysis parameters.

At least one embodiment of the invention furthermore relates to a method for calibrating an X-ray detector, wherein a first and second set of count rates are generated for a detection unit on the basis of the switchover from first to second signal analysis parameters. The expression "calibrating an X-ray detector" relates in particular to the acquisition of calibration data which is used in the course of an X-ray measurement or an image reconstruction. For example, this can relate to calibration parameters for data preprocessing or image reconstruction, such as for linearity correction, flat field correction, beam hardening correction, or similar, for example.

BRIEF DESCRIPTION OF THE DRAWINGS

The invention is explained once again in more detail hereinbelow with the aid of example embodiments and with reference to the attached figures. Like components are labeled with identical reference numerals in the various figures, in which.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

According to at least one embodiment of the invention, a quanta-counting or photon-counting X-ray detector comprising a detection unit is proposed which generates a detection signal on the basis of X-ray radiation incident on the detection unit. The detection unit comprises in particular a detection zone in order for example to generate charge pulses as a detection signal for X-ray radiation absorbed by the detection unit. The detection signal and in particular the charge pulses are therefore suitable in particular for determining the energy of the absorbed X-ray radiation.

The detection zone or a detection surface can be a semiconductor material directly sensing or absorbing X-ray radiation (direct converter).

It is also conceivable for the detection zone to include a scintillator material which converts X-ray radiation into radiation in other, in particular visible, spectral ranges. The converted radiation can be detected via a semiconductor detector, for example a photodiode or a silicon photomultiplier, positioned in the radiation path downstream of the scintillator and generally likewise incorporated in the detection unit. The photodiode, the silicon photomultiplier or the semiconductor detector then generates a detection signal which can also be analyzed with regard to the spectral distribution and intensity of the X-ray radiation detected by the scintillator.

The X-ray detector according to at least one embodiment of the invention additionally has a signal analysis module which determines a set of count rates for X-ray radiation incident on the detection unit or at least partially absorbed by the detection unit on the basis of the detection signal and predefined signal analysis parameters for X-ray radiation, in particular in a quanta- or photon-counting manner. In this case the set of count rates generally comprises, as mentioned in the introduction, a plurality of count rates which are determined simultaneously for a single detector channel, preferably for a single projection. The count rates determined simultaneously for a single detector channel are determined with respectively assigned different energy threshold values, in particular for a plurality of energy thresholds.

The signal analysis module can be integrated in particular into a device called an ASIC (Application-Specific Integrated Circuit) or realized in the structural form of an ASIC. In particular the detection unit and at least parts of the signal analysis modules can be incorporated in the detector channel referred to in the introduction.

The term "signal analysis parameters" is used in the following to signify not only parameter values, such as the energy threshold values for example, but also parameters themselves, such as the energy thresholds for example, insofar as no distinction is explicitly made between the two cases.

The signal analysis parameters can be energy threshold values, for example, or even the number of assigned energy thresholds, which accordingly define or modify the determination of the set of count rates. The signal analysis parameters can for example be stored in a so-called configuration register of the ASIC.

The X-ray detector according to at least one embodiment of the invention additionally has a switchover control unit for switching between first signal analysis parameters and second signal analysis parameters, such that, given a specific, i.e. identical, amount of X-ray radiation incident on the detection unit, a first set of count rates is generated on the basis of first signal analysis parameters for a first time interval beginning at a first time instant, and given predefined second signal analysis parameters different from predefined first signal analysis parameters, a second set of count rates, preferably different from the first set, is generated for a second time interval beginning at a second time instant.

With the aid of the switchover unit it is therefore possible to switch quickly, in particular after a frame time, between different signal analysis parameters. In other words, the first signal analysis parameters are included in a first set of signal analysis parameters used for the analysis of the detection signal prior to the switchover, while the second signal analysis parameters are incorporated in the (then second) set of signal analysis parameters used for the analysis of the detection signal only after the switchover. In particular the second signal analysis parameters can replace the first signal analysis parameters in the set of signal analysis parameters that is used.

In this context the first and second signal analysis parameters can in each case also be a single value or parameter. The first signal analysis parameters can for example comprise first energy threshold values and the second signal analysis parameters second energy threshold values which are at least partly different from the first energy threshold values. By means of a fast, in particular cyclic switchover between the first and second energy threshold values it is possible in particular to increase the number of energy thresholds checked preferably for one projection beyond the number that is limited for example by the quantity of comparators for energy thresholds present in a detector channel. The resolution of the projection measurement data can therefore be increased in a simple manner with regard to the energy of the detected X-ray radiation.

It should be explicitly mentioned here that the switchover according to at least one embodiment of the invention takes place at least between first and second signal analysis parameters. Over and beyond this, further, third, fourth or more sets of signal analysis parameters can also be used for the switchover, with the result that third, fourth or more sets of count rates are generated.

Also proposed according to at least one embodiment of the invention is an X-ray imaging system, in particular a CT system, having an X-ray source for emitting X-ray radiation and an inventive X-ray detector for detecting the X-ray radiation emitted by the X-ray source.

At least one embodiment of the invention furthermore relates to a method for determining count rates for X-ray radiation by use of an X-ray detector, wherein the signal analysis module is used to generate a first set of count rates for X-ray radiation incident on the detection unit using, i.e. on the basis of, first signal analysis parameters, and in a following step a switchover of the signal analysis module is effected, preferably for the purpose of acquiring an, in particular immediately, succeeding projection, to second signal analysis parameters which are different from the first signal analysis parameters.

In at least one embodiment of the method, the signal analysis module determines a second set of count rates for X-ray radiation incident on the detection unit on the basis of, i.e. using, the second signal analysis parameters, which second set of count rates is preferably different from the first set of count rates for identically embodied X-ray radiation incident on the detection unit.

At least one embodiment of the invention furthermore relates to a method for calibrating an X-ray detector, wherein a first and second set of count rates are generated for a detection unit on the basis of the switchover from first to second signal analysis parameters. The expression "calibrating an X-ray detector" relates in particular to the acquisition of calibration data which is used in the course of an X-ray measurement or an image reconstruction. For example, this can relate to calibration parameters for data preprocessing or image reconstruction, such as for linearity correction, flat field correction, beam hardening correction, or similar, for example.

As already mentioned, the number of energy thresholds checked in particular for one projection during the calibration method can therefore be increased beyond the number of comparators for energy thresholds present, thereby enabling the calibration parameters or calibration data to be located particularly quickly. As a result the calibration method as a whole is speeded up.

Other particularly advantageous embodiments and developments of the invention will emerge from the dependent claims as well as from the following description, wherein the independent claims of one claims category can also be developed analogously to the dependent claims of another claims category.

In a development of at least one embodiment of the invention, the start of the first time interval, i.e. the first time instant, and the start of the second time interval, i.e. the second time instant, are separated from each other by a time gap of between 100 µs and 1 ms, i.e. preferably in a frame time.

If, for example, X-ray projection methods entailing a high rotational speed of the gantry, such as a flash method for example, are employed, it can be beneficial in particular if the first signal analysis parameters are used for analyzing X-ray radiation of a first projection and, following switchover, the second signal analysis parameters are used for a projection or frame acquired immediately thereafter in time, such that the X-ray radiation of the two projections acquired immediately succeeding one another in time is analyzed using different signal analysis parameters.

In particular, the switchover unit can be embodied for cyclic, preferably alternating switchover between the first signal analysis parameters and the second signal analysis parameters. In this case the switchover can take place at periodic time intervals, i.e. a temporal "interlacing" of signal analysis parameters used for analyzing the detection signal is proposed in this development.

Furthermore, the switchover unit can also be embodied for so-called stochastic switchover, i.e. in the sense of non-regular switchover. For example, the switchover can also take place randomly or pseudorandomly, i.e. without a fixed cycle. This is particularly advantageous when working with more than two sets of signal analysis parameters.

For that purpose, the X-ray detector can for example have a memory unit for simultaneously storing the first signal analysis parameters and the second signal analysis parameters. In this way a plurality of sets of signal analysis parameters for the signal analysis parameters of one transmission channel in each case, i.e. in particular of different energy threshold values, can be stored or made available for the energy thresholds of one transmission channel. It is clear in this case that the number of sets of signal analysis parameters does not have to be limited to two. Preferably up to sixteen different sets of signal analysis parameters which can be used in the method according to the invention can be stored in the memory unit simultaneously.

Typically, one or more different configuration registers providing a storage location for said signal analysis parameters are available in an ASIC. In this context a distinction can be made between different types of configuration registers. A first type of configuration registers is provided for example for global signal analysis parameters, i.e. for parameters that are valid for all detection units of the detector. Another type of configuration registers is available for local signal analysis parameters, which are specified separately for each detection unit. The latter often include for example the energy thresholds or energy threshold values that are predefined at a specific time instant for a specific detection unit.

It should be explicitly emphasized that preferably a plurality of storage locations are made available per signal analysis parameter, with preferably each of the global and in particular local signal analysis parameters used at a specific time instant being in each case stored more than once and at least in part differently in the storage locations or configuration registers.

It should furthermore be mentioned in this context, that this constitutes a difference as compared with the reconfiguration of the ASIC, in which the signal analysis parameters would have to be read into the ASIC via an interface at each switchover. Typically, the detection unit acquires projection measurement data continuously. In other words, a reconfiguration or new configuration of the ASIC would have to be performed during said measurement. In order to avoid a signal distortion due to high electrical activity of the ASIC, the development having a plurality of dedicated storage locations in the X-ray detector for one of the signal analysis parameters in each case is particularly advantageous. A further advantage compared to a reconfiguration lies in the fact that the switchover between two sets of signal analysis parameters can be accomplished very quickly, i.e. in particular significantly faster than the time taken for a reconfiguration, which is generally between 3 ms and 4 ms. In other words, the switchover can in this case be effected faster than a frame time.

The memory unit can in particular be connected to an interface in order to read at least some of the cited signal analysis parameters into the X-ray detector or, as the case may be, into the memory unit. These are therefore variable signal analysis parameters or sets of signal analysis parameters.

As mentioned, the switchover of the signal analysis parameters can take place cyclically, particularly preferably in a maximum of sixteen cycles, i.e. using a maximum of sixteen sets of count rates or signal analysis parameter sets which, as explained, can be stored in the memory unit simultaneously. Particularly preferably the switchover is performed in an alternating manner such that the acquisition of the X-ray projection data is not significantly extended by the switchover method, and for example the rotational speed of the gantry can be maintained virtually unchanged.

The switchover unit can additionally have an initiating interface or trigger interface for receiving a trigger signal for triggering the switchover. For example, various concepts using temporal interlacing are known in X-ray imaging, which are applied in order to increase the spatial resolution of an X-ray detector. With the aid of the trigger interface, these proposals can be combined with the inventive concept for increasing the energy or intensity resolution. One proposal for increasing the spatial resolution relates to the cyclic variation of the focus spot of the X-ray source between different locations. This method is known for example as "flying focus spot". With the aid of the trigger interface, a synchronization can take place between the cyclic variation of the focus spot and the cyclic switchover of the signal analysis parameters used, such that the two concepts can be combined with each other.

Another proposal for increasing the energy resolution of the X-ray detector relates to the technique known as "fast kV switching". This entails a cyclic switching between different spectra of the X-ray radiation of an X-ray source. With the aid of the trigger interface, this switching of the X-ray spectra can also be synchronized in time with the switchover between different sets of signal analysis parameters, i.e. the switchover between first and second signal analysis parameters.

Furthermore, a gantry angle or projection-angle-dependent trigger signal can be acquired with the aid of the trigger interface. It is equally conceivable for the trigger signal to be generated by an external timer which, for example, as mentioned, can operate pseudorandomly. It is also conceivable for already existing signals, particularly advantageously the signal defining the frame time, to be used for triggering a switchover.

As mentioned, the signal analysis parameters can relate inter alia to energy threshold values or to the number of energy thresholds used. In addition it is also conceivable for so-called "signal shaping parameters" such as a "shaping time", for example, a so-called "undershoot" or else a so-called "gain" to be included in the signal analysis Parameters.

The "shaping time" (also: "peaking time") is the time during which the charge carriers generated in the detector can make a contribution to the pulse shape of an individual detection pulse. As mentioned, the detection signal is typically a charge or current pulse which is converted into a voltage pulse with the aid of the analysis module. The "shaping time" therefore relates to a period of time in which, in order to generate a single voltage pulse, charge is collected on the detection surface and the voltage pulse is shaped. Typically, the "shaping time" lies in the range between 5 ns and 1 µs, i.e. the shaping time is much smaller than the frame time.

The so-called "undershoot" is a voltage value to which the generated voltage signal decays before it returns to its bias level. The undershoot can be used in particular to improve the signal separation of different voltage pulses succeeding one another at short time intervals.

The amplification factor or "gain", as it is called, determines the relationship between the accumulated charge or input current intensity and the level of the corresponding voltage pulse. It therefore determines the maximum output signal level, i.e. for example at the output of the amplifier, that is reached in the amplification of a current pulse.

With the aid of the described signal shaping parameters it is possible in particular to choose between a preference toward a precise charge measurement and a preference toward a precise separation of X-ray quanta. If, for example, a long shaping time is chosen, a precise charge measurement can be made and consequently a precise energy determined. In other words, the preference in this case is toward a precise determination of the X-ray spectrum. However, in situations where it is necessary to analyze a high number of X-ray quanta virtually simultaneously, i.e. in the so-called "high flux case", it is not always possible with a long shaping time to separate the resulting pulses for X-ray quanta succeeding one another immediately in time. Such situations are referred to as "pile-up events", where the generated voltage pulses of absorbed X-ray quanta immediately succeeding one another can no longer be separated from one another. This means in particular that the number of "pile-up events" can be set by way of the cited shaping time. If the number of "pile-up events" is reduced, for example by means of a short "shaping time" for the high flux case, this can nonetheless lower the precision of the charge measurement with the generated voltage pulse. This is what is referred to as the "ballistic deficit". The choice of a specific "shaping time" is consequently always a compromise between achievable charge separation charge separation, i.e. measurement of the X-ray intensity, and Precision of the charge determination, i.e. measurement of the spectral distribution of the X-ray radiation.

Over and above the possibility of predefining a specific compromise, the switchover of the shaping time enables adaptation to different cases for absorbed X-ray radiation, such that at different time instants (the first or second time instant) it is namely possible to shift the compromise from optimal charge determination, successively, to optimal signal separation. In this way it is possible to combine a precise charge measurement for a frame with a precise signal separation (i.e. only few pile-up events). Different contrast information and hence different image characteristics can thus be set and generated "quasi simultaneously".

The signal analysis parameters can furthermore include detection signal combination parameters, such as the so-called "charge summing mode" of an X-ray detector, for example. In this case the detection signals of a plurality of detection units are combined with one another so that a common set of count rates is determined for a combined detection signal. Typically, the absorption of an X-ray quantum is a cascade process in which one or more fluorescence photons are released which for example can be scattered into a neighboring pixel or an adjacent detection unit. This applies in particular in the case of so-called subpixelated detectors which possibly have no septa (anti-scatter grid) between the detection zones of neighboring subpixels. Under certain conditions it is thus possible, through combination of the signals of a plurality of pixels (or subpixels), to obtain a more accurate result for the charge determination. For example, a summation signal of a four-group of adjacent detection units can be combined and output in the form of the analog signal (charge pulse) of the detection unit. The detection signal present in the form of the summation signal is then analyzed by the analysis module as described with the aid of signal analysis parameters, such as signal shaping parameters or energy threshold values, for example, in the form of count rates and output as a set of count rates.

With the aid of the targeted adaptation of the signal analysis parameters it is possible, as explained, to achieve different optimization goals in terms of the quality of the X-ray imaging or the analysis of X-ray radiation. The invention enables in particular the virtually simultaneous pursuit of a plurality of different optimization goals. The first signal analysis parameters can be adapted in particular to a first type of desired image characteristics, and the second signal analysis parameters to a second type of image characteristics different therefrom. The image characteristics can relate in particular to the contrast, the definition and the spatial resolution of the X-ray projection data. Thus it is possible, for example, to adapt the first signal analysis parameters to a desired iodine contrast, i.e. in particular the energy threshold values can be suitably chosen, and the second signal analysis parameters to a desired tissue contrast, for example for cardiac tissue.

Thus it is possible, for example, to add additional contrasts and i.e. in particular additional definition to the X-ray projection data beyond the number of energy thresholds Predefined by the hardware and to derive suitable image information.

Figure 1:
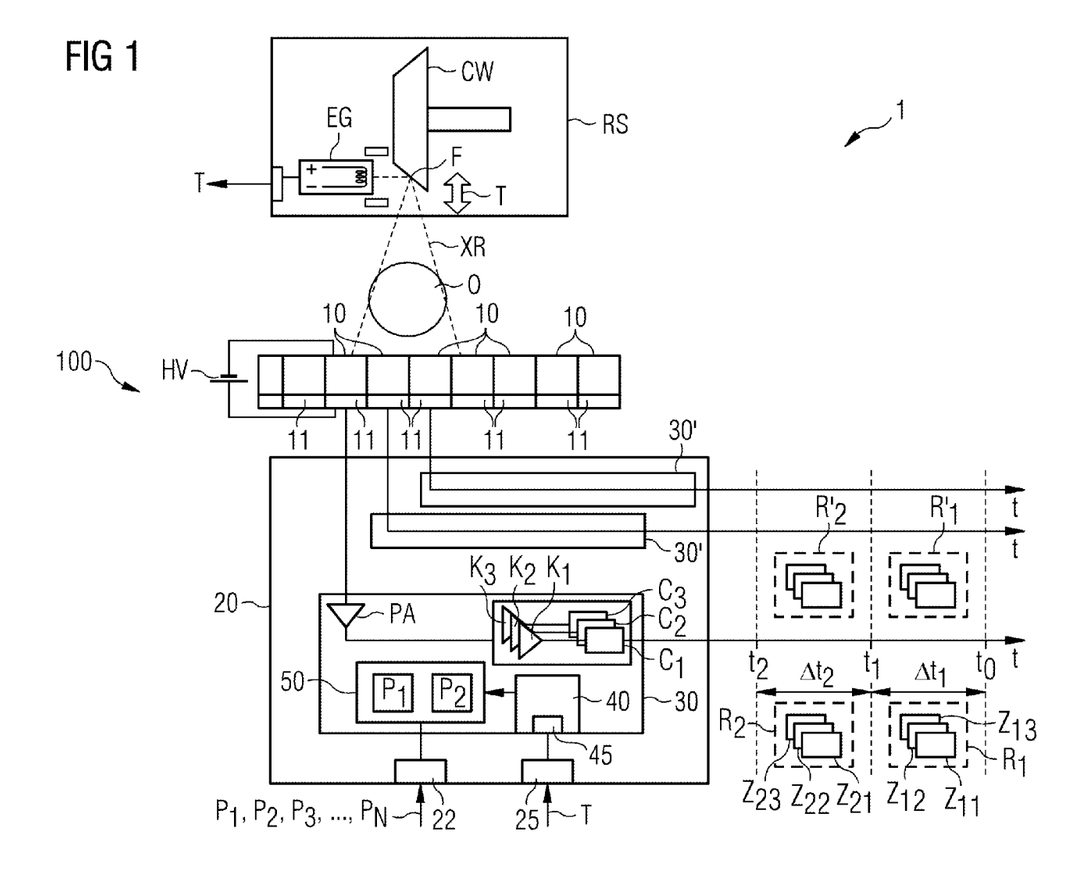
FIG. 1 shows an example embodiment of an X-ray imaging system having an X-ray source and an example embodiment of an X-ray detector according to the invention.

FIG. 1 shows a computed tomography system 1 having an X-ray source RS which emits X-ray radiation XR that is detected by an X-ray detector 100 positioned opposite the X-ray source RS. An examination object O, referred to hereinbelow as patient O for short, is arranged between the X-ray source RS and the X-ray detector 100. The patient O is irradiated by the X-ray radiation XR so that the projection measurement data of the X-ray detector 100 can be used for the reconstruction of image data of the examination object. The X-ray detector 100 according to the invention comprises a plurality of detection units 10 which are arranged adjacent to one another in a planar array and which are in each case connected to a signal analysis module 30, 30'. The detection units 10 are also referred to hereinbelow as pixels for short. The signal analysis modules, 30, 30' are combined in an application-specific circuit (ASIC) 20.

Only the signal analysis module 30 is considered in more depth below by way of example. However, the signal analysis modules 30' can essentially have the same design and mode of operation as the signal analysis module 30, so a more detailed description of the signal analysis modules 30' can be dispensed with.

The detection unit 10, formed in the present case by means of a direct-converting semiconductor element, based on Cd(Zn)Te for example, generates a current pulse for absorbed X-ray quanta of the X-ray radiation XR under the influence of a high voltage HV that is applied between electrodes 11 of the detection unit 10, which current pulse is made available as a detection signal to the signal analysis module 30. It should be mentioned in this context that usually the backside electrode is embodied as a common electrode 11 for all detection units 10. Said detection signal is analyzed using a set of signal analysis parameters $P_1$ that is valid in each case at a specific time instant $t_0$ for a specific time interval $\Delta t_1$. To that end the current pulse is converted by the analysis module 30 into a voltage pulse corresponding to the energy of the absorbed X-ray quantum. This is accomplished with the aid of a preamplifier PA, taking into account the signal analysis parameters $P_1$. The generated voltage pulse is translated with the aid of a plurality of comparators $K_1$, $K_2$, $K_3$ and respectively assigned counters $C_1$, $C_2$, $C_3$ into a set of count rates $R_1$. In this case each comparator $K_1$, $K_2$, $K_3$ is assigned a separate energy threshold having in each case an energy threshold value as one of the signal analysis parameters $P_1$. On the basis of the first signal analysis parameters $P_1$ a first set of count rates $R_1$ is thus generated with the aid of the comparators, said first set in each case including a count rate $Z_{11}$, $Z_{12}$, $Z_{13}$ for each of the comparators $K_1$, $K_2$, $K_3$ that are connected to a detection unit 10.

At a second time instant $t_1$ the switchover takes place to second signal analysis parameters $P_2$ or to a second set of signal analysis parameters which includes the second signal analysis parameters $P_2$ for the first time after the switchover, which parameters $P_2$ are in turn valid for a second time interval $\Delta t_2$. The X-ray quanta or detection signals analyzed in this time interval are evaluated on the basis of the second signal analysis parameters $P_2$. A switchover between the first signal analysis parameters $P_1$ and the second signal analysis parameters $P_2$ can be effected with the aid of a memory unit 50 which simultaneously stores the first signal analysis parameters $P_1$ and the second signal analysis parameters $P_2$. At the time of the switchover parameters can therefore be transmitted quickly from the memory unit 50, which in this example embodiment is integrated in the signal analysis module 30, to corresponding computing units of the signal analysis module 30 or, as the case may be, to the preamplifier and/or to the comparators $K_1$, $K_2$, $K_3$, such that these can operate on the basis of the second signal analysis parameters $P_2$. It should be emphasized in this context that in addition the memory unit 50 can also store further sets of signal analysis parameters $P_3, \ldots, P_N$, between which it is possible to switch when necessary, as described.

For the second time interval $\Delta t_2$ a second set of count rates $R_2$ is thus generated which in turn includes a count rate $Z_{21}$, $Z_{22}$, $Z_{23}$ for each of the comparators $K_1$, $K_2$, $K_3$ assigned to a detection unit 10. The first and second signal analysis parameters $P_1$, $P_2$ can be transmitted to the memory unit 50 via a configuration interface 22 of the ASIC 20 for example prior to the start of an X-ray measurement that is to be carried out.

The further signal analysis modules 30' assigned in each case to other detection units 10, as is indicated merely schematically, are operated coordinated in time with the signal analysis module 30 likewise with different first and second signal analysis parameters, i.e. a temporally coordinated switchover between first and second signal analysis parameters takes place in the case of the other signal analysis modules 30'. As is likewise indicated schematically, in the first time interval $\Delta t_1$ the further signal analysis modules 30' generated a first set of count rates $R_1'$ using first signal analysis parameters, and in the second time interval $\Delta t_2$ a second set of count rates $R_2'$ using second signal analysis parameters different from the first signal analysis parameters, which second set in turn includes a count rate for each comparator of the signal analysis unit 30'.

In the illustrated example embodiment the computed tomography system 1 is embodied for performing a method known as "kV switching". This entails cyclically switching over the acceleration voltage of an electron source EG incorporated in the X-ray source RS, producing a radical increase in the spectral performance of the X-ray source RS as a result of switching over between a plurality of X-ray spectra compared with operation using a continuous acceleration voltage. In this case a trigger signal T is generated at each switchover.

Furthermore, the computed tomography system 1 is also embodied to apply a method according to the so-called "flying focus spot" concept. This entails spatially varying the position of the X-ray focus F on a rotating crown wheel CW, as is indicated schematically by the arrow. A trigger signal T is likewise generated with each variation. In this variation the distance of the X-ray focus from the surface of the X-ray detector 100 is varied so that different angles of incidence are generated for the generated X-ray radiation XR as a function of the focus position in order to improve the spatial resolution of the detector. Both methods utilize the cyclic switchover of control parameters of the X-ray source, such as focus position or acceleration voltage. Said cyclic switchover can be synchronized by means of the trigger signal T, for example, with the switchover of signal analysis parameters.

For this purpose the trigger signal T can be transmitted via a control interface 25 of the ASIC 20 to a trigger interface 45 of a switchover control unit 40, for example. The switchover control unit 40 is embodied to instruct the memory unit to transmit first signal analysis parameters $P_1$ or second signal analysis parameters $P_2$ to an evaluation unit of the signal analysis module 30. The switchover can be effected at periodic or cyclic time intervals or else on the basis of the trigger signal T.

Figure 2:
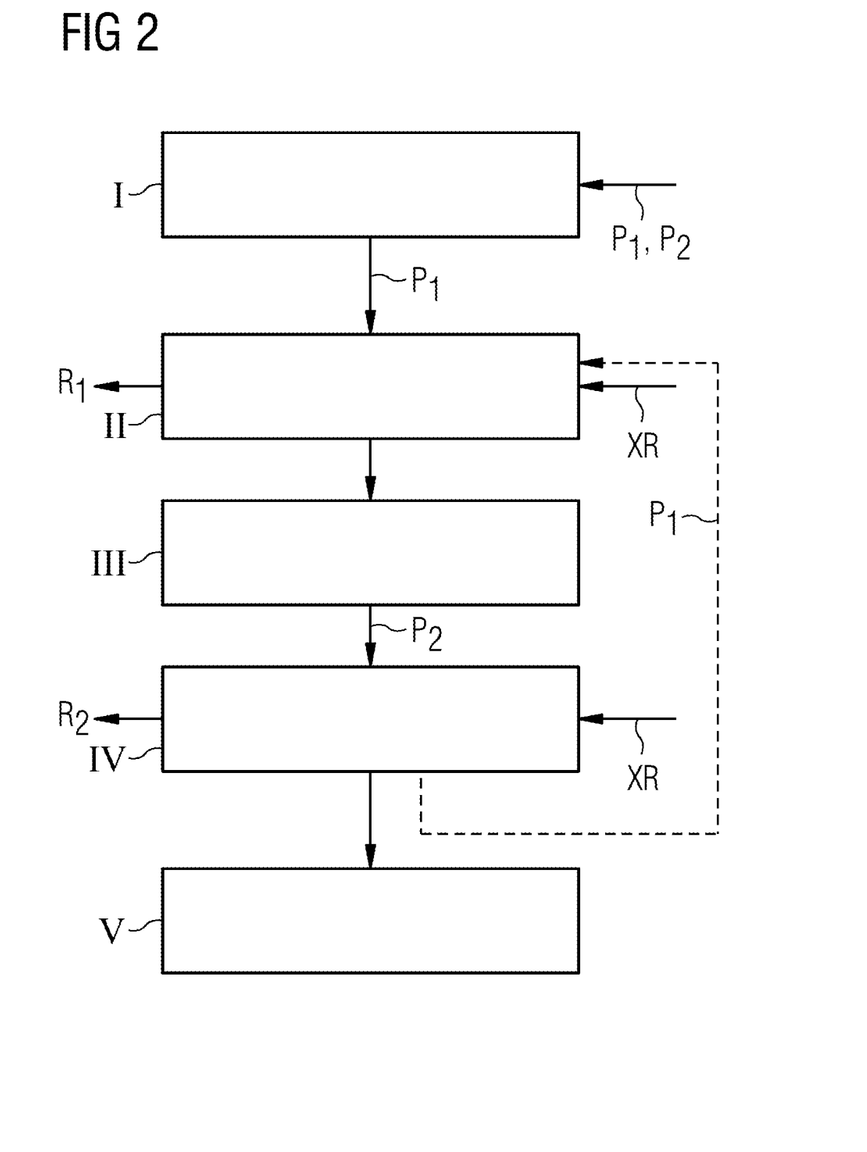
FIG. 2 shows a method for determining count rates.

The exact sequence of steps in the cyclic switching is described in detail for example in a method according to FIG. 2. In an initial step I, first signal analysis parameters $P_1$ and second signal analysis parameters $P_2$ are read into the memory unit so that these are stored simultaneously in the memory unit. This enables the choice or switchover between first signal analysis parameters $P_1$ and second signal analysis parameters $P_2$. In a following step II, the first signal analysis parameters $P_1$ are used in order to analyze a detection signal for X-ray radiation XR incident on the detection unit. A first set of count rates R1 is determined for the incident X-ray radiation XR in a first assigned time interval using the first signal analysis parameters $P_1$. In a following step III, a switchover is made to second signal analysis parameters $P_2$. After the switchover, in step IV, a second set of count rates $R_2$ for X-ray radiation XR incident on the same detection unit for which the first set of count rates $R_1$ was determined is determined using the second signal analysis parameters $P_2$. As mentioned, this switchover between first signal analysis parameters $P_1$ and second signal analysis parameters $P_2$ can take place cyclically. The switchover between first and second signal analysis parameters $P_1$, $P_2$ can be performed for example after the acquisition of a first projection at a first projection angle and before the immediately succeeding acquisition of a second projection at a different, second projection angle. The switchover is therefore effected between the first frame time and the second frame time.

A reiteration of the method beginning with step II (after a further switchover to the first set of signal analysis parameters $P_1$) is then performed starting at an in turn different, third projection angle after a further frame time. It is therefore unnecessary to reload the first and second signal analysis parameters $P_1$, $P_2$ into the memory unit because these are still available in the memory unit, such that after the generation of the second set of count rates $R_2$ X-ray radiation XR incident on the detection unit is again evaluated using first signal analysis parameters $P_1$ and a first set of count rates $R_1$ is generated once again, albeit for a projection acquired at a third projection angle.

In the reiteration, the method is continued at least up to step IV and a reiteration can be performed until such time as, for example, all projections required for the reconstruction of the desired sectional images or of the volumetric dataset have been acquired. The thus generated projection measurement data can then be used in step V for the reconstruction of image data. Alternatively it is also conceivable that in step V, for example, the calibration of an X-ray detector is performed using the thus generated projection measurement data. For example, the X-ray radiation can be a predefined amount of X-ray radiation defined without an examination object being present between X-ray source and detection unit. Accordingly, calibration data can be determined for example in a step V on the basis of the projection measurement data and used in a subsequent reconstruction of image data. Thus, a particularly fast determination of the calibration parameters is possible in the event that the first and second signal analysis parameters $P_1$, $P_2$ comprise a plurality of different energy thresholds.

Figure 3:
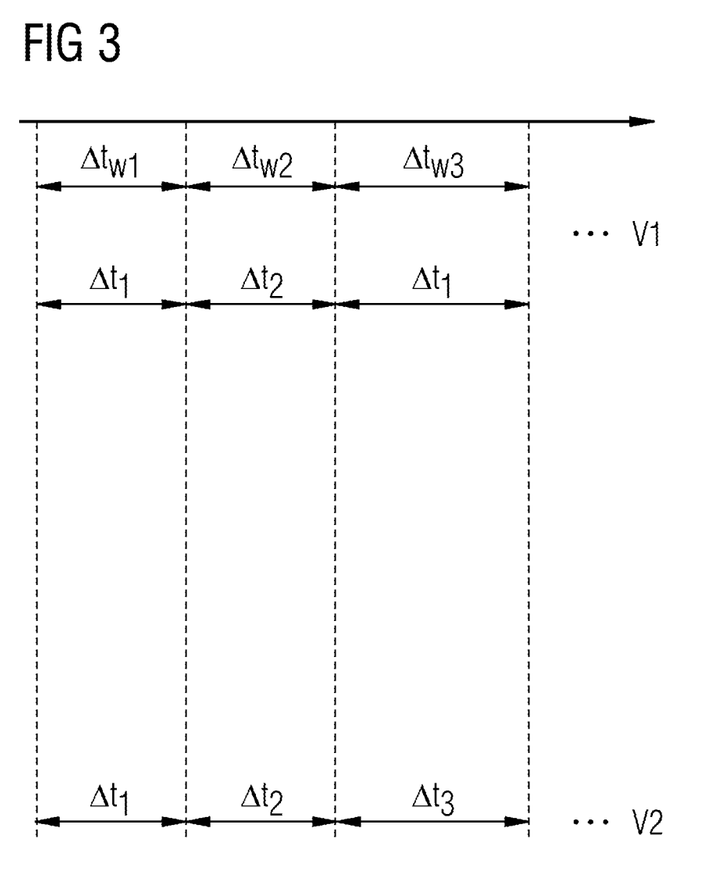
FIG. 3 shows a timing diagram for several variants of the switchover between first signal analysis parameters and second signal analysis parameters.

How the first time interval and the second time interval are arranged in the total period of time required for acquiring a frame or an image is clear from FIG. 3.

FIG. 3 shows several variants V1, V2 illustrating how a first time interval $\Delta t_1$ and a second time interval $\Delta t_2$ or even a third time interval $\Delta t_3$, for each of which a separate set of count rates is generated, can be organized in time in relation to the acquisition of the individual projections. A different set of signal analysis parameters can be used as described in each of the time intervals.

In this regard, FIG. 3 shows in extract form several angle projection times $\Delta t_{w1}$, $\Delta t_{w2}$ and $\Delta t_{w3}$, each corresponding to a frame time. In a first variant V1, the first time interval $\Delta t_1$ corresponds to a first angle projection time $\Delta t_{w1}$, and the second time interval $\Delta t_2$ to a second angle projection time $\Delta t_{w2}$ in which a second projection is acquired. The time intervals $\Delta t_{w1}$ and $\Delta t_1$ are in each case synchronized with the acquisition of a new projection at a different projection angle, i.e. the switchover between different signal analysis parameters $P_1$ and $P_2$ in each case takes place synchronously in time with the acquisition of a new projection.

As can be seen in a second variant V2, the switchover is not just limited to a change between first signal analysis Parameters $P_1$ and second signal analysis parameters $P_2$. For example, instead of the alternating switchover according to variants V1 or V2, the switchover can also be effected with a greater number of three or more cycles and three or more sets of different signal analysis parameters.

In this case the second variant V2 corresponds to a modification of variant $V_1$. Here, third signal analysis parameters can be assigned to a third time interval $\Delta t_3$, i.e. the signal analysis module operates in the time period $\Delta t_3$ with third signal analysis parameters. Accordingly, the only difference between the second variant V2 and the first variant V1 is that the number of cycles in which a switchover takes place is not limited to two, but instead three cycles are used in this case.

In order to avoid a situation in which the time intervals $\Delta t_1$, $\Delta t_2$ assigned to specific signal analysis parameters $P_1$, $P_2$ could be too small in relation to the total scan duration of the CT scan, or alternatively the consequence could be a drastic increase in the required total scan duration, the detector can be limited to switching over between a maximum of sixteen cycles, i.e. a maximum of sixteen different sets of signal analysis parameters.

Figure 4:
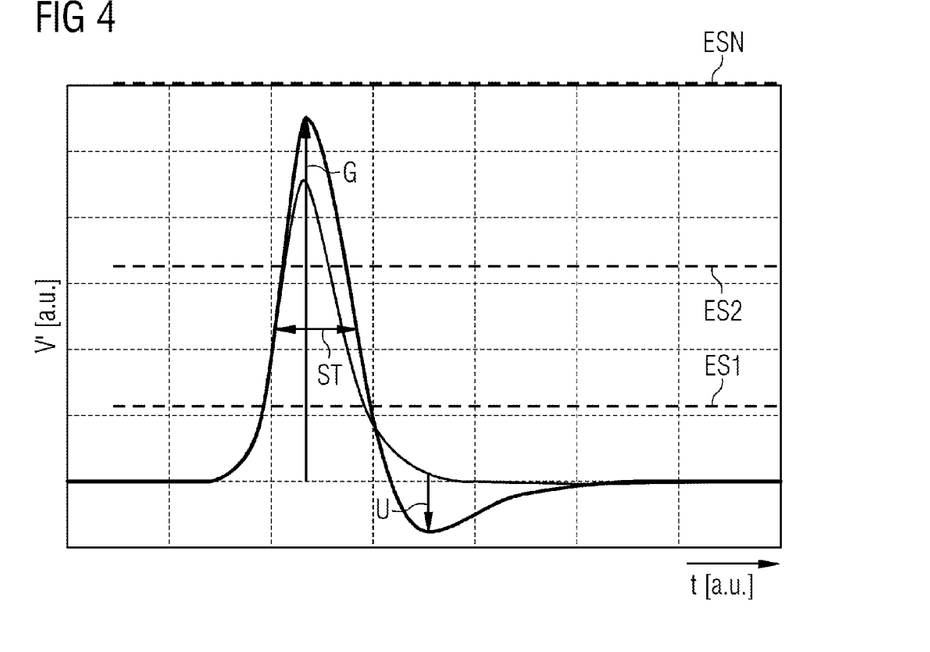
FIG. 4 shows the variation with time of a generated voltage signal generated using a plurality of signal analysis parameters.

FIG. 4 shows a number of possible signal analysis parameters selected for the switchover in detail. In this case a signal generated by the signal analysis unit from a charge pulse in the form of a voltage pulse for detecting an X-ray quantum is shown. The amplified signal voltage, i.e. the output signal level, is shown in arbitrary units (a.u.) in the vertical axis, which signal voltage is determined with the aid of an integration or convolution of the current pulse generated by the detection unit. The variation with time (in arbitrary units—a.u.) of said voltage signal is shown on the transverse axis. The signal analysis parameters include for example the so-called gain G, which specifies the maximum signal level in relation to a standard signal. The signal analysis parameters can also include the so-called shaping time ST, which in this case is assumed as the full width at half maximum of the voltage pulse. In addition, the so-called undershoot U, i.e. the magnitude of the signal decay or size of the negative voltage according to the signal-related representation of the X-ray quantum in the form of a voltage pulse, can also be set, by means of which a temporal signal separation of a plurality of X-ray quanta can be identified. In addition, the signal analysis parameters also include a number N of energy thresholds, where N typically lies between two and eight, to each of which an energy threshold value ES1, ES2, . . . , ESN is assigned for which a separate count rate value is generated in the set of count rates.

Figure 5:
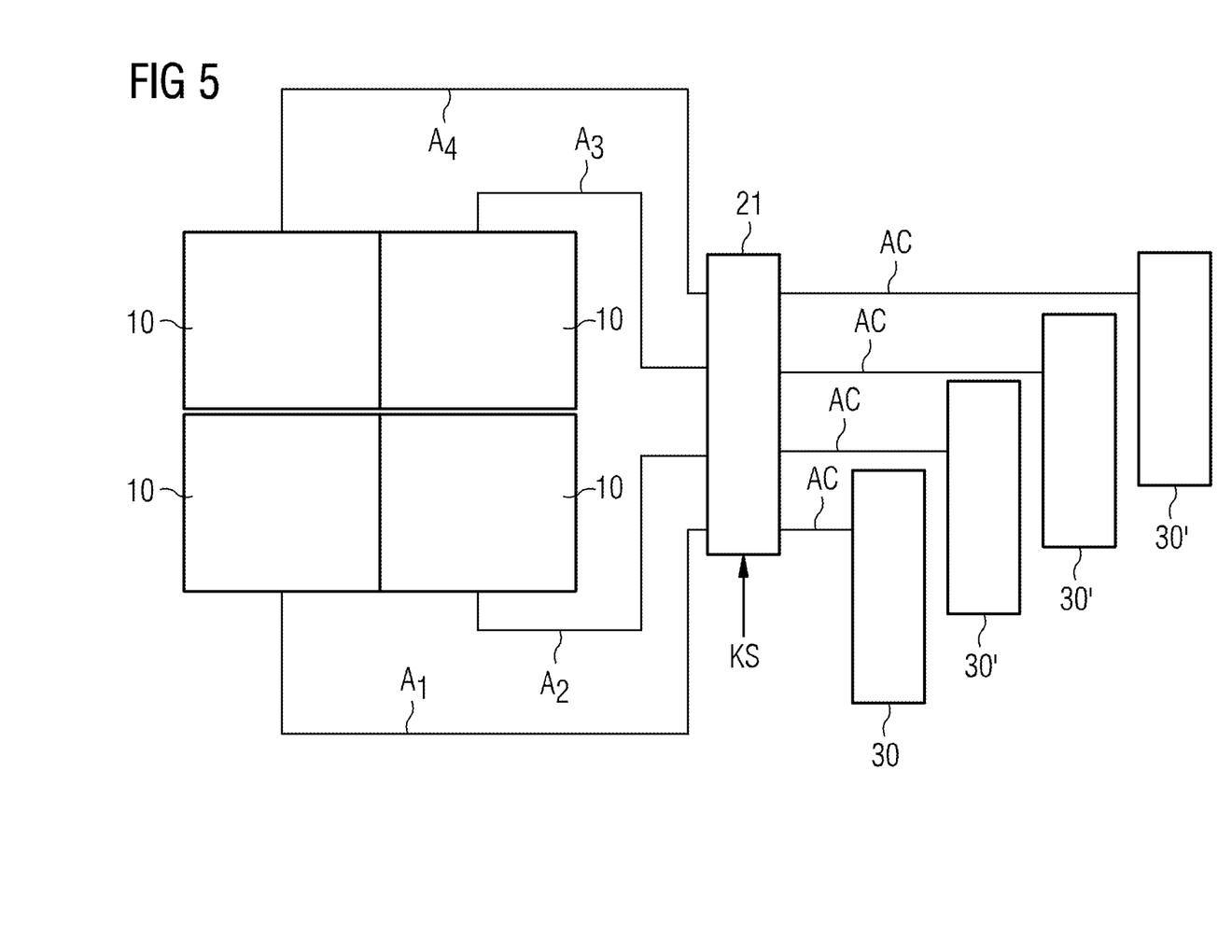
FIG. 5 shows an example embodiment for the activation and deactivation of a "charge summing mode".

FIG. 5 additionally shows further possible signal analysis parameters which can be included in the switched-over first and/or second signal analysis parameters. FIG. 5 shows an X-ray detector comprising neighboring detection units 10, called pixels, arranged adjacent to one another in the manner of a matrix. In the absorption of X-ray radiation it can happen due to secondary effects such as e.g. fluorescence radiation that an X-ray quantum excites charge pulses not only in a single detection unit 10, but also in a plurality of neighboring detection units 10. The charge generated in a detection unit 10 consequently does not correspond to the X-ray energy of the X-ray quantum. In order to suppress this effect in the determination of the count rates, a so-called charge summing mode, for example, can be activated with the aid of an activation signal KS. Toward that end the detection signals $A_1$, $A_2$, $A_3$, $A_4$ of a plurality of the neighboring detection units 10 are combined in a signal combination unit 21 to form a common signal AC. Said signal is passed on as combination signal AC to a signal analysis module 30 which in normal operation is assigned to that pixel which contributes the most to the charge summing signal in this case. The other signal analysis modules 30' connected to the signal combination unit 21 receive no signal AC in this case. In this example embodiment the signal AC is routed by way of example to the signal analysis module 30. It is equally conceivable that any other of the signal analysis modules 30, 30' will be selected in the above-described manner by the signal combination unit 21 to receive the signal AC. Such a signal combination unit 21 is generally provided for each crossing point of a plurality of pixels. Consequently, each signal analysis unit 30, 30' assigned to a specific pixel has a corresponding combination input to which a plurality of signals are supplied, each of which is generated at a crossing point at the edge of a pixel (each corner) with the aid of a signal combination unit 21 in each case. The typical method of operation of the charge summing mode is described for example in the journal IEEE Trans. Nucl. Sci. NS-54 (2007) 1824: "The Medipix3 Prototype, a Pixel Readout Chip Working in Single Photon Counting Mode With Improved Spectrometric Performance" by Ballabriga, R., Campbell, M., Heijne, E. H. M., Llopart, X., and Tlustos, L. The signal combination unit 21 can be included as a discrete structural unit, for example in the ASIC described with reference to FIG. 1 (FIG. 1, 20), though it can also be arranged inside one or more detector units 10. Furthermore, it is also conceivable that the signal combination unit 21 is incorporated in the signal analysis module 30, 30'. In the illustrated example embodiment it can therefore also be varied as an occasionally used signal analysis parameter whether the described charge summing mode is activated or deactivated, i.e. a value of the activation signal KS.

Preferred sets of first and second signal analysis parameters comprise, for example, parameter sets which are optimized with regard to spectral resolution and other parameter sets which are optimized with regard to a high flux case.

The optimization can be carried out in particular with regard to an intrinsic pulse width of an influenced signal at the electrode of the detection unit detecting X-ray radiation as cited with reference to FIG. 1. Said intrinsic pulse width is typically a constant of the detection unit and is permanently predefined by the design of the detection unit or electrodes. In most cases the intrinsic pulse width lies in the range between 2 ns and 70 ns.

The optimization can furthermore be carried out with regard to the cited gain, which determines the number of X-ray photons whose accumulated detection signals can be simultaneously amplified without distortion in the cited Preamplifier. This number is determined by the dynamic range of the amplifier and a photon energy predefined for said number as well as by the gain G. The following applies to the number n:

$$n = \max(\text{dynamic range})/G \cdot \text{photon energy}.$$

A set of first or second signal analysis parameters optimized with regard to spectral resolution could be specified as follows:
- long shaping time (full width at half maximum) of, for example, more than ten times the intrinsic pulse width,
- no undershoot (undershoot=0V),
- charge summing mode activated,
- high gain
- With a high gain G (unit mV/keV), n is less than or equal to three. The predefined photon energy can be, for example, the maximum energy of the emitted X-ray radiation, or else be defined by other factors such as a desired contrast, for example. With regard to the dynamic range it should furthermore be noted that in this case only the dynamic range that is available for acquiring a dynamic signal is taken into account, and for example almost constantly amplified leakage currents occurring in the detection unit can determine the limits of this available dynamic range.
- energy thresholds of, for example, 25, 30, 60, 80 keV optimized for low flux contrast.

A set of first or second signal analysis parameters optimized with regard to intensity determination could be specified as follows:
- short shaping time of, for example, less than three times the intrinsic pulse width cited with reference to the long shaping time,
- pronounced undershoot of more than 5% of the maximum value of the corresponding generated detection pulse (V),
- charge summing mode deactivated,
- low gain of, for example, more than n=10 (cf. definition of "high gain"),
- optimized energy thresholds which, for the pile-up case, include an energy threshold which is greater than the maximum energy of an X-ray quantum generated by the X-ray source at the detection time instant, for example 25, 60, 80, 160 keV.

Preferably, one or more energy thresholds are identical for the high flux case and the low flux case. With the aid of said identical energy threshold it would thus be possible to determine the deformation of the X-ray spectrum due to the pile-up events.

In the case of the first and/or second set of signal analysis parameters, the energy thresholds could be optimized with regard to the acquisition of specific contrasts, for example for acquiring contrast information for iodine, bone, soft tissue, or a multi-energy contrast for different material bases such as $H_2O$, I, GD, AU, etc.

The switchover between different sets of signal analysis parameters enables the temporal switchover between different types of image characteristics, i.e., as mentioned, different contrast renditions in the measurement data, for example. In this case, as mentioned, in particular the spectral resolution, but also the intensity measurement of the detected X-ray radiation, can be improved. As a result, X-ray imaging as a whole can be improved by optimized projection measurement data.

It should be pointed out in this context that the features of all example embodiments or of developments disclosed in figures can be used in any combination. It is also pointed out in conclusion that the X-ray detector described in detail hereinabove, the imaging system, the method for determining count rates and the method for calibrating signal analysis parameters are merely example embodiments which can be modified in a multiplicity of different ways by the person skilled in the art without leaving the scope of protection of the invention. For example, the X-ray detector can also be embodied as an annular detector which completely encloses a measurement space of an imaging system in one direction. Furthermore, the use of the indefinite article "a" or "an" does not exclude the possibility that the features in question may also be present more than once.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Although the invention has been illustrated and described in greater detail by the preferred example embodiment, the invention is not restricted by the disclosed examples and other variations can be derived therefrom by the person skilled in the art, without departing from the scope of protection of the invention.

What is claimed is:

1. An X-ray detector, comprising:
   a detection unit, configured to generate a detection signal for X-ray radiation incident on the detection unit;
   a signal analysis module, configured to determine a set of count rates for X-ray radiation incident on the detection unit on the basis of the detection signal and signal analysis parameters for X-ray radiation; and
   a switchover control unit, configured to switch between at least first signal analysis parameters and second signal analysis parameters such that when an amount of X-ray radiation is incident on the detection module, a first set of count rates being generated for a first time interval on the basis of first signal analysis parameters, and a second set of count rates being generated for a second time interval on the basis of second signal analysis parameters, different from the first signal analysis parameters, the first and second signal analysis parameters being either signal shaping parameters or detection signal combination parameters.

2. The X-ray detector of claim 1, wherein a start of the first time interval and a start of the second time interval are separated by a time gap of between 100 μs and 1 ms.

3. The X-ray detector of claim 2, wherein the switchover unit is configured for cyclic switchover between the first signal analysis parameters and the second signal analysis parameters.

4. The X-ray detector of claim 3, wherein the switchover unit is configured for alternating switchover between the first signal analysis parameters and the second signal analysis parameters.

5. The X-ray detector of claim 2, further comprising:
   a memory unit, configured to simultaneously store the first signal analysis parameters and the second signal analysis parameters.

6. An X-ray imaging system, comprising:
   an X-ray source; and
   the X-ray detector of claim 2.

7. The X-ray detector of claim 1, wherein the switchover unit is configured for cyclic switchover between the first signal analysis parameters and the second signal analysis parameters.

8. The X-ray detector of claim 7, wherein the switchover unit is configured for alternating switchover between the first signal analysis parameters and the second signal analysis parameters.

9. The X-ray detector of claim 1, further comprising:
   a memory unit, configured to simultaneously store the first signal analysis parameters and the second signal analysis parameters.

10. The X-ray detector of claim 1, wherein the switchover unit includes a trigger interface, configured to receive a trigger signal for triggering the switchover.

11. An X-ray imaging system, comprising:
    an X-ray source; and
    the X-ray detector of claim 1.

12. The X-ray imaging system of claim 11, wherein the X-ray imaging system is a CT system.

13. The X-ray detector of claim 1, wherein the a switchover control unit, configured to switch between at least first signal analysis parameters and second signal analysis parameters, configures the detector to switch between the first and second signal analysis parameters to allow for a relatively more precise measurement of electrical charges or one of a relatively more precise separation of x-ray quanta and a charge summing mode.

14. A method for determining count rates for X-ray radiation of an X-ray detector including a detection unit for generating a detection signal for X-ray radiation incident on the detection unit, the method comprising:
    generating, via signal analysis module, a first set of count rates for X-ray radiation incident on the detection unit on the basis of first signal analysis parameters;
    performing a switchover of the signal analysis module to second signal analysis parameters, different from the first signal analysis parameters; and
    determining, via the signal analysis module, a second set of count rates for X-ray radiation incident on the detection unit on the basis of the second signal analysis parameters, the first and second signal analysis parameters being either signal shaping parameters or detection signal combination parameters.

15. The method of claim 14, wherein the switchover is performed cyclically.

16. The method of claim 15, wherein the switchover is performed cyclically in a maximum of sixteen cycles.

17. The method of claim 16, wherein the switchover is performed cyclically in a maximum of sixteen cycles, in an alternating manner.

18. The method of claim 14, wherein the switchover takes place at least one of
  in synchronism with the switchover of an X-ray spectrum of an X-ray source, and
  in synchronism with the switchover of the focus position of an X-ray source.

19. The method of claim 14, wherein the first signal analysis parameters are adapted to a first type of desired image characteristics, and the second signal analysis parameters are adapted to a second type of desired image characteristics, different from the first type of desired image characteristics.

20. The method of claim 14, wherein the switchover is performed to switch between the first and second signal analysis parameters to allow for a relatively more precise measurement of electrical charges or one of a relatively more precise separation of x-ray quanta and a charge summing mode.

* * * * *